(12) United States Patent
Benes et al.

(10) Patent No.: US 6,241,961 B1
(45) Date of Patent: Jun. 5, 2001

(54) RADIOIMMUNO CONJUGATES FOR USE IN HUMAN THERAPY AND METHOD FOR THEIR PREPARATION

(76) Inventors: Ivan Friedrich Benes, Im Dornacher 7, 8127 Forch (CH); Klaus Bosslet, Minheimer Strasse 6, 13465 Berlin Frohnau (DE)

(*) Notice: Subject to any disclaimer, the term of this patent is extended or adjusted under 35 U.S.C. 154(b) by 0 days.

(21) Appl. No.: 09/280,028

(22) Filed: Mar. 26, 1999

(30) Foreign Application Priority Data

Mar. 27, 1998 (DE) .............................................. 198 13 687
Mar. 15, 1999 (DE) .............................................. 199 11 329

(51) Int. Cl.[7] .......................... A61K 51/00; A61M 36/14
(52) U.S. Cl. .................. 424/1.49; 424/1.11; 424/141.1; 424/130.1; 424/9.1; 530/388.1
(58) Field of Search ................... 424/1.11, 1.37, 424/1.41, 1.49, 1.53, 1.57, 1.69, 1.81, 9.1, 141.1, 130.1, 133.1, 134.1, 1.35, 136.1, 142.1, 153.1, 155.1; 530/387.1, 387.2, 388.1, 388.15

(56) References Cited

U.S. PATENT DOCUMENTS 4,986,979 * 1/1991 Morgan, Jr. et al. ................ 424/1.11
5,180,816 * 1/1993 Dean .................................... 530/404
5,273,738 * 12/1993 Matthews et al. .................. 424/1.11

* cited by examiner

Primary Examiner—Dameron L. Jones
(74) Attorney, Agent, or Firm—Henry M. Feiereisen; Ursula B. Day

(57) ABSTRACT

The invention relates to a type of radioimmuno-conjugates where the α-radiators or the β-radiators are stably coupled to the antibody with or without the use of a complex-forming agent and wherein the radioisotope is not iodine and wherein the β-radiators are Yttrium-90, Rhenium-188, Rhenium-186, Copper-67, Holmium-166 and Samarium-153 and the α-radiators are Astatine-211 or Bismuth-212 and wherein the MAb-moiety of the conjugate is derived either from the mouse, a human or other mammal and which can be either intact, fragmented, humanized or recombinantly manipulated. Furthermore, the invention relates to radioimmuno-conjugates where the MAb binds onto an extracellular antigen, which preferentially appears on cells of the haematopoietic system or where the MAb binds to an antigen at the surface of granulocytes or granulocyte-precursors, or both of these cell types, or were the MAb moiety of the conjugate binds onto an epitope or epitopes of CD 66, respectively CD 66 a, b, c and e. Furthermore, the invention discloses the use of radioimmuno conjugates for the depletion of bone marrow either as monotherapy or as an adjunct to chemotherapy and/or whole body irradiation and bone marrow transplantation.

10 Claims, No Drawings

RADIOIMMUNO CONJUGATES FOR USE IN HUMAN THERAPY AND METHOD FOR THEIR PREPARATION

CROSS-REFERENCES TO RELATED APPLICATIONS

This application claims the priorities of German Patent Application, Serial Nos. 198 13 687.0, filed Mar. 27, 1998 and 199 11 329.7, filed Mar. 15, 1999, the subject matter of which is incorporated herein by reference.

BACKGROUND OF THE INVENTION

The present invention relates in general to radioimmuno conjugates and in particular to radioimmuno conjugates of the type to be used in the therapy of human patients for the treatment of malignant haematopoietic diseases. The invention relates furthermore to a method for preparing the radioimmuno conjugates.

In modern therapy, two types of treatments are normally applied with malignant haematopoietic diseases: In one type of treatment, high doses of differentiated chemotherapy is followed by bone marrow and/or stem cell transplantation. In the other type of treatment, high doses of differentiated chemotherapy and whole body irradiation is followed by bone marrow and/or stem cell transplantation. The goal of the aggressive, high-dose and mostly differentiated chemotherapy or radiation of the full body which is carried out with energy rich, hard gamma rays (e.g. high voltage therapy with a $^{60}$Co-Cobalt-source), or a combination of the two therapies, is to kill the malignant cells as well as their precursor cells generated in surplus in the bone marrow. This is preferably done in a quantitative or semi-quantitative manner already at the level of their common pluripotent stem cells. This procedure also causes the destruction of the blood forming-, granulocyte producing—as well as the thrombocyte forming—system in the bone marrow and without any further therapeutic measures, this strong immuno suppression would lead unequivocally to the patient's death. Only immediate intravenous injection of bone marrow suspensions and/or suspensions of allogenic stem cells or, whenever possible, suspensions of autologous bone marrow and purified bone marrow obtained through purging techniques, guarantees the survival of the patient. The cells which are intravenously supplied, subsequently settle in the lymphoid organs such as the bone marrow and the spleen. A few weeks after the patient has undergone chemotherapy and/or full body radiation during which the patient's haematopoiesis was destroyed, these cells, by virtue of undergoing mitosis, differentiation and maturing, develop into fully functioning blood components such as erythrocytes, granulocytes, thrombocytes, myelocytes, monocytes. Administration of these intensive therapies has resulted in a markedly improved survival rate of those patients suffering from various malignant haematopoietic diseases.

Such therapies have however, various shortcomings. In addition to the destruction of haematopoisis and the serious changes induced by the immuno suppression, there are also additional side effects caused by the highly concentrated chemotherapy and/or whole body radiation which causes further damage to other essential organs. Such organ damage manifests itself for example in hair loss, nausea, vomiting and general malaise of the patient.

In addition to such observed side effects as kidney-toxicity (Mirabell et al. J. Clin. Oncol. 1996, 14 (2) 579–585), cataracts (Alevard T. Acta Oncol. 1996, 35 (7) 137–140), germ cell dysfunction (Sarafoglou et al. J. Pediatr. 1997, 130 (2) 210–216) which occur with high frequency, there were also cases where acute respiratory system threatening noninfectious epiglottitis has occurred (Murray et al. Bone Marrow Transplantation 1995, 15 (6) 997–998).

Numerous patients with malignant haematopoietic diseases are children making it thus an even more urgent medical need to improve the treatments so there are fewer side effects and also in particular, to improve their efficacy.

Within the last fifteen years, a number of experiments have been carried out using unlabeled monoclonal antibodies (MAb) and/or radio-labeled monoclonal antibodies (radio immune conjugates) in order to improve the treatment of malignant diseases. It was only within the past five years that the clinical efficacy of unlabelled cytotoxic MAb could be shown. Thus, Riethmüller et al. (Lancet 1994, 343 1177–1183) could show ascertainable statistics in life prolongation with a cytotoxic, non genetically-engineered MAb from a mouse used in a randomized clinical study during the treatment of "minimal residual disease" in colon carcinoma.

So far, the clinical efficacy of unlabelled MAb has not yet been shown in the treatment of larger tumor masses, even though, in addition to the MAb from the mouse, humanized and genetically engineered MAbs and their fragments have also been used. (Colnaghi et al. Current Opinion in Oncology 1993, 5, 1035–1042). For this reason, a number of researchers have tried to radio label MAb as well as their gene-technological variants of different specificity, origin and size, such as for example cytostatic agents or radioactive isotopes (Courtenay-Luck and Epenetos, Immunology 1990, 2 880–883). In order to bind the toxic components at the MAb, divers coupling and labeling methods were used.

Only in the past several years, suitable radionuclides with advantageous radiation properties, such as for example, Phosphorus-32, Strontium-89, Yttrium-90, Samarium-153, Erbium-169, Ytterbium-175, Rhenium-188 were successfully and stably coupled to MAb for therapeutic purposes by means of bi-functional complex forming agents (while iodine has been known for many years to couple to MAb, it is not particularly useful because of its unfavorable radiation properties).

Radiochemical methods for labelling MAb using various radionuclides are divided into two groups: the direct labeling methods and the indirect labeling methods. With the direct method, the inner di-sulfide bonds (—S—S—) of the hinge-region of the MAb are being partially reduced to sulfhydril groups (—SH). To do this, various chemical compounds having reducing properties are used, such as for example, the derivatives of ascorbic acid (Hnatowich D. et al. J. Nucl. Med. 1994; 35: 127–134), and/or substances with sulfhydryl groups or stannic-II-compounds or complexes (Mather S. et al. J. Nucl. Med. 1990; 31: 692–697, Paik C et al J. Nucl. Med. Biol. 1985; 12: 3–8, Rhodes B. J. Nucl. Med. 1986: 27: 685–693, Thakur M. et al. Nucl. Med. Biol. 1991; 18: 227–233, Schearz A. et al. J. Nucl. med. Biol. 1986: 28: 721). Experiments to couple Re-186 or Re-188 stably onto a MAb without using complex forming agents, have led to the formation of conjugates, according to the present level of knowledge (Visser et al. J. Nucl. Med. 1993, 3, 1953–1963, see page 1962, lines 34–38) that are not sufficiently stable (Griffiths et al. Cancer Res. 1991, 51, 4594–4602, Su et al. J. Nucl. Med. 1992, 33, 910).

In the indirect labeling methods of MAb, mostly bi-functional complex forming agents are used, such as diamine-dithiol (Baidoo K. et al. Cancer Res. 1990: 50: 799–803), or a bi-functional ester of NHS-BAT (Eisenhut M. et al. J Nucl Med 1991; 37: 362–370), or diamiddimercaptid (Kasina S. et al. J. Nucl. Med. 1991; 32: 1445–1451) and/or DTPA (Najafi A. et al. Int. J. Appl. Radiat. Isot. 1984; 5: 554–557), or a novel complex forming agent, which is based upon a N2S4-composition (Najafi A. et al. Nucl. Med. Biol. 1991; 18: 179–185, Qu T. et al. Radiochim. Acta 1993; 63: 209–212) for conjugating the radionuclide onto the MAb. Alternative methods which facilitate an indirect coupling (conjugation) of the radionuclide to the MAb are based on the conjugation of thiolgroups to amino acids (e.g. lysine) in the protein molecule with 2-iminothiolan (Joiris E. et al. Nucl. Med. Biol. 1991, 18: 353–356) or with the groups of 1-imino-4-mercaptobutyl compounds (Goedemans W. in Nicolin M. et al. (eds.) Verona 1990; 595–603).

Suitable complex forming agents for the complex formation, especially with Yttrium (preferably Y-90) are, for example, DOTA (Denora et al. Anticancer Research 1997, 17, 1735–1744) or 12 N4-maleimid (tetra-azocyclododecantextra-acetic acid) (Turner et al. Br. J. Cancer, 1994, 70: 35–41, and King et al. Cancer Research, 1994, 54: 6176–6185). Particularly suited for complex formation of Rhenium (preferably Re-186 or Re-188), is for example, the MAG-3 complex forming agent (van Gog et al. J. Nucl. Med. 1996, 37, (2), 352–362). These methods suffer, however, from the disadvantage that an immuno response may be formed against the complex-forming portion of the MAb-complex forming conjugate. Thus, none of the prior known methods have produced a satisfactory conjugate for the treatment of malignant haematopoietic diseases. Furthermore, the available therapies for treating the aforementioned highly malignant haematopoietic diseases is unsatisfactory due to the massive side effects they provoke. It was therefore an object of the inventors to develop a novel radioimmuno conjugate for use in treating these diseases which by its application would replace, or at a minimum reduce the need for numerous applications of high dose chemotherapy or total body irradiation.

SUMMARY OF THE INVENTION

It is thus an object of the present invention to provide an improved radioimmuno conjugate, obviating the aforestated drawbacks.

It is another object of the present invention to provide such radioimmuno conjugates that are preferred in the treatment of haemopoietic diseases, and also to treat various tumors and inflammations.

It is a still another object of the present invention to provide an improved radioimmuno conjugate according to the invention with which an improved treatment, in particular, for haemopoietic diseases can be administered and to replace the high dose chemotherapy and total body irradiation.

It is a still another object of the present invention to provide an improved radioimmuno conjugate according to the invention wherein the magnitude as well as the frequency of occurring side effects is lower than with the standard high dose chemotherapy and whole body radiation.

These objects, and others which will become apparent hereinafter, are attained in accordance with the present invention by providing a radioimmuno conjugate for use in therapy wherein α-radiators or β-radiators preferably Rhenium, Yttrium, Samarium or others, are coupled to the MAb without the use of complex forming agents.

It is a feature of the radioimmuno conjugates according to the invention as compared to the complex forming agents described in the relevant literature, that these conjugates do not induce an immuno response against the complex forming agent.

Another feature of the radioimmuno conjugates according to the present invention is their high stability which make them particularly suited for use in therapeutic applications as compared to those radioimmuno conjugates known in the literature that are synthesized without complex forming agents, It is a further feature of the invention that use of the conjugates according to the invention in monotherapy of acute and chronic myeloid leukemia leads to a very successful treatment of these diseases. Furthermore, it has been shown that the conjugate according to the invention is successfully used in the treatment not only in application of monotherapy but also in conjunction with targeted chemotherapy or total body irradiation that are used in treating acute and chronic lymphatic leukemias and lymphomas.

Therapeutic applications of the radioimmuno conjugates according to the invention have also been extended into broader applicability of the conjugates in conjunction with ligands that are known form the literature as having specificity for lymphocytic antigens such as CD 19, CD 20 CD 22, HLL 2 and HLA DR 10 β. Another area of application, the conjugates according to the invention are therapeutically applied in the area of bi-specific antibody radioimmuno conjugates in accordance with Example 14, infra having specificity against granulocytic antigens and lymphocytic antigens.

In accordance with further findings, these bi-specific antibody radioimmuno conjugates can be therapeutically applied, in accordance with Example 14, infra when combined with specificities such as CD 19, anti CD 20, anti CD 22, anti HLA DR 10β or HLL 2.

A further therapeutic application of the radioimmuno conjugates according to the invention with the granulocytic and lymphocytic antigens has been found in the use of complex forming agents in the form of soluble salts, as set forth in detail further below.

A further advantageous application of the radioimmuno conjugates according to the invention has been shown to be in their use as two-phase-radioimmuno conjugates, consisting of a biotinylated MAb and avidin labeled with α- or β-radiators used in therapeutic treatment of malignant haemotopoietic diseases. Moreover, the two-phase radioimmuno conjugates consisting of biotinylated MAb with α- or β-radiators labeled avidin bonding molecules such as streptoavidin or its recombinant, biochemically or peptide chemically engineered fragments have been successfully applied in therapy of malignant, haemotopoietic diseases.

DETAILED DESCRIPTION OF THE INVENTION

The above and other objects, features and advantages of the present invention will now be described in more detail with reference to the following description.

The synthesis of the radioimmuno conjugate conforms to the examples as recited below wherein the antibodies used react with cells of the haematopoietic system, such as for example, granulocytes, granulocyte-precursors or both types of cells. Especially suited are antibodies which react with CD 66, such as for example, the MAb as disclosed in the Sequence Listing which reacts with CD 66 a, b, c and e. The specificity of its V-region is defined through its cDNA sequence disclosed in the Sequence Listing.

EXAMPLES

Example 1

A MAb of the type having a V-region as disclosed in the Sequence Listing is purified, stabilized and sterilized by filtration and provided as a clear filtrate. The MAb is calibrated to a MAb concentration of 1 mg MAb/ml with a sterile phosphate buffer solution. The solution is then partially concentrated by means of an ultrafiltration unit to a volume of $\leq 200$ ml and subsequently freed from the stabilizers through dia-filtration under addition of phospate buffer and brought to a volume of 200 ml.

To the so purified and partially concentrated MAb, 2-mercaptoethanol is added in a ratio of 1000:1 mole (mercaptoethanol:MAb) and under slight stirring for 30 minutes at room temperature, the MAb is partially reductively split. After the reaction time, the surplus of mercaptoethanol is diafiltrated by repeated diafiltration with 200 ml of a sterile, filtrated nitrogen-saturated phophate buffer solution under constant control of the residual content of 2-mercaptoethanol. A limit value of <1 $\mu$g/ml must be reached. The resulting antibody concentration was then determined, which serves as the basis for the calibration of the MAb final concentration (2.0 mg/ml) as well as the basis for the addition of the stabilizer (2 mg Sorbitol pro 1 mg MAb) in the final solution. The clear, sterile, filtrated and saturated with sterile filtrated nitrogen final solution, is then ready to be filled immediately, under GMP conditions, into glass vials that have been washed, depyrogenated and sterilized, to a filling weight of 500±10 mg, and filled by automation each into an injection bottle which has been cooled with liquid nitrogen. Subsequently, the vials are closed with stoppers used for freeze drying and then freeze dried under automatic control of a lyophilization program and placed under airtight condition in a protective nitrogen atmosphere.

The labeling of the lyophilized MAb with the $\beta$-radiator, for example the radionuclide Rhenium-188, which is used in the chemical form of sodiumperrhenal, is carried out with the MAb directly in the vial after the MAb has been reduced and lyophilised. First, a solution, containing a complex of a sensitive reducing agent consisting of tetra-natriil, 1,3,3-propane-tetra-phosphonas in the form of a stannic (II) complex (0.5 mg:0.06 mg) is added to the lyophilised MAb, which mildly regulates the reducing action of the MAb. Thereafter, the solution of the $^{188}$Re-sodium-perrhenate having the desired activity in the range of from 1.85–7.4 GBq ($\cong$50–200 mCl), or that of another $\beta$-radiator is added. The $^{188}$Re-sodiumperrhenate solution was previously freshly eluated from a $^{188}$W-wolfram/$^{188}$Re-Rhenium-generator with a 0.9% sodium chloride solution.

Example 2

A MAb of the type having a V-region as disclosed in the Sequence Listing is purified, stabilized and sterilized by filtration and provided as a clear filtrate. The MAb is calibrated to a MAb concentration of 1 mg MAb/ml with a sterile phosphate buffer solution. The solution is then partially concentrated by means of an ultra filtration unit to a volume of $\leq 200$ ml and subsequently freed from the stabilizers through dia-filtration under addition of phosphate buffer to a volume of 200 ml. The purified and partially concentrated MAb which is in a glass container is recirculated by means of a rubber tube pump coupled to silicon connection tubes which are connected to a flat flow-through quartz cuvet (volume 3 ml). The MAb solution which circulates within this closed system is kept continuously under a circulating sterile nitrogen gas atmosphere. Within the area of the quartz glass cuvet, is a closed, shielded quartz lamp system which is equipped with 2 compact HQT-Halogen-metal vapor-UV-high pressure quartz bulbs (capacity per bulb 150 W, type: TS 150 W/NDL, manufactured by Osram-Germany). The UV radiation intensity in the center of the cuvet is 625±10 $\mu$W cm$^{-2}$. The top output of the UV spectrum of these UV radiators is in the wavelength range between 250–260 nm, on average at 254 nm (80%). Smaller percentages are of the following wavelengths, 295 nm (1%), 365 nm (3%), 410 nm (2%), 470 nm (7%), 510 nm (1%) and 545 nm (6%). In this closed system, the circulating MAb solution is exposed for 30 minutes to the UV radiation under formation of H-radicals. In this reaction, the di-sulfide-bonds (—S—S—) in the heavy chains of the immunoglobulins are reduced to sulfhydril groups (—SH), whereby a direct coupling of radionuclides is achieved.

The further process steps such as the formulation, the stabilizing, the aseptic filling, the steps to the pharmaceutical preparation, lyophilisation as well as the labeling with radionuclides of the pharmaceutical preparation suitable for injection, in particular labeling with $\beta$-radiators, preferably Yttrium-90, Strontium-89, Samarium-153, Rhenium-186, Rhenium-188, is carried out in the same manner as described in Example 1.

Example 3

As an alternative to the use of tetranatrii-1,1,3,3-propane tetra phosphonas-stannic (II)-complex, the reduced MAb as in example 1 and 2 is treated with a complex of ethylene diamine-N,N,N',N'-tetrakis-[methylenphosphonas stannic (II)] as a soft reducing agent, then binding and/or coupling it to a radionuclide, preferably a $\beta$-radiator, such as Yttrium-90, Strontium-89, Samarium-153, Rhenium-186, Rhenium-188 as described in Example 1.

Example 4

As an alternative to the use of tetranatrii-1,2,3,3-propane tetra phosphonas-stannic (II)-complex, the reduced MAb, of Example 1 and 2 is treated with a complex of diethylene-triamine penta-[methylenphosphonas stannic (II)] as a soft reducing agent and then reacted and/or coupled to a radionuclide, preferably a $\beta$-radiator, such as Yttrium-90, Strontium-89, Samarium-153, Rhenium-186, Rhenium-188 as listed in example 1.

Example 5

As an alternative to the use of tetranatrii-1,2,3,3-propane tetra phosphonas-stannic(II)-complex, the reduced MAb of Example 1 and 2 is treated with a complex of dicitrate-tri-stannic (II)-complex as a soft reducing agent and then reacted and/or coupled to a radionuclide, preferably a $\beta$-radiator, such as Yttrium-90, Strontium-89, Samarium-153, Rhenium-186, Rhenium-188 as listed in Example 1.

Example 6

A MAb of the type having a V-region as disclosed in the Sequence Listing, is purified, stabilized and sterilized by filtration and provided as a small filtrate. The MAb is calibrated with a sterile phosphate buffer solution, for example to a MAb concentration of 1 mg MAb/ml The solution is then partially concentrated by means of an ultrafiltration unit to a volume of $\leq 200$ ml and subsequently, freed from the stabilizers through dia-filtration, under addition of phosphate buffer, brought to volume of 200 ml.

To the so purified and partially concentrated MAb, 2,3-dihydroxy-2-cyclopenten-1-one is added in the same manner as in Example 1 in a ratio of 500:1 mole and under slight stirring, and under supplying nitrogen gas, reacted for 20 minutes at room temperature. Thereby, the di-sulfide bridges (—S—S—) of the MAb's hinge region are partially reduced and transformed into reactive sulfhydryl groups (—SH). The surplus of 2,3 di-hydroxy-2-cyclopenten-1-one is not removed but serves as a stabilizer for the reduced MAb and later on participates in the coupling of a radionuclide (e.g. Yttrium-90, Rhenium-186, Rhenium-188 and others) to the sulfhydryl groups of the MAb. The resulting antibody concentration of the MAb solution is determined by measuring the extinction-coefficient, which serves as a basis for calculating the calibration of the final concentration (2.0 mg/ml) and the addition of the stabilizer (2.0 mg/ml sorbitol per 1 mg MAb).

The further process steps of the formulation, the stabilizing, the aseptic filling, and the steps to the pharmaceutical preparation, lyophilization as well as the labeling with radionuclides the pharmaceutical form for injection, in particular, labeling with β-radiators, preferably with Yttrium-90, Strontium-89, Samarium-153, Rhenium-186, Rhenium-188 is carried out in the manner as described in Example 1.

Example 7

A MAb of the type having a V-region as disclosed in Sequence Listing, is purified, stabilized and sterilized by filtration and provided as a small filtrate. The MAb is calibrated with a sterile phosphate buffer solution, for example to a MAb concentration of 1 mg MAb/ml. The solution is then partially concentrated by means of an ultrafiltration unit to a volume of ≦200 ml and subsequently, freed from the stabilizers through diafiltration, and under addition of phosphate buffer brought to volume of 200 ml.

To the so purified and partially concentrated MAb, 5-methyl-2,3-dihydroxy-2-cyclopenten-1-one is added in the same manner as in Example 1 in a ratio of 300:1 mole and, under slight stirring and under supplying nitrogen gas, reacted for 20 minutes at room temperature. Thereby the disulfide bridges (—S—S—) of the MAb's hinge region are partially reduced and transformed into reactive sulfhydryl groups (—SH). The surplus of 5-methyl-2,3-dihydroxy-2-cyclopenten-1-one is not removed but serves as a stabilizer for the reduced MAb and later on participates in the coupling of a radionuclide (e.g. Yttrium-90, Rhenium-186, Rhenium-188 and others) to the sulfhydryl groups of the MAb. The resulting antibody concentration of the MAb solution is determined by measuring the extinction-coefficient which serves as a basis for calculating the calibration of the final concentration (2.0 mg/ml) and the addition of the stabilizer (2.0 mg/ml sorbitol per 1 mg MAb).

The further process steps of the formulation, the stabilizing, the aseptic filling, and the steps to the pharmaceutical preparation, lyophilisation as well as the labeling with radionuclides of the pharmaceutical form, for injection, in particular, labeling with beta radiators, preferably with Yttrium-90, Strontium-89, Samarium-153, Rhenium-186, Rhenium-188 is carried out in the manner as described in Example 1.

Example 8

The MAb of the type as described in Examples 1, 2, 6 and 7 but which has not been previously reduced, advantageously, the MAb with the specificity as disclosed in the Sequence Listing is combined with an α-amino-β-methyl-β-mercaptobutyric acid-stannic (II)-complex which behaves like a reducing agent but simultaneously also like a complex forming agent, with the result, that the MAb and the radionuclide are reduced, simultaneously binding the radionuclide to the MAb. In this reaction, a radionuclide of the type such as Yttrium-90, Strontium-89, Samarium-153, Rhenium-186, Rhenium-188 is used which is provided in 7-valent form as, for example, [188]Re-sodiumperrhenate (NaReO$_4$) is used.

Example 9

The MAb of the type as described in Examples 1, 2, 6 and 7 but which has not been previously reduced, advantageously, the MAb with the specificity as disclosed in Sequence Listing, is combined with a mercapto-succinic acid-stannic(II)-complex which behaves like a reducing agent but simultaneously also like a complex forming agent, with the result, that when combined, the MAb and a radionuclide are being reduced and simultaneously, the radionuclide binds to the MAb. In this reaction, a radionuclide of the type such as Yttrium-90, Strontium-89, Samarium-153, Rhenium-186, Rhenium-188 provided in 7-valent form, as for example, 188Re-sodiumperrhenate (NaReO4) is used.

After the radioimmuno conjugate labeled with Rhenium-188 has been intravenously administered to the patient, the following relative distribution of radioactivity is observed:

Liver: 8%
Lung: 2%
Spleen: 6%
Kidneys: 4%
Bone Marrow: 80%

This distribution pattern proves, that the Re-88 conjugate of a suitable MAb specific against granulocytes and bone marrow stem cells, such as for example, the MAb with a V-region as disclosed in the Sequence Listing, is capable of irradiating the basal cells and the lymphoid organs (specifically the bone marrow) by way of either, a strong local dose and/or in fractionated doses, by way of single doses of activity. Accordingly, with the aid of this radioimmuno conjugate, a complete elimination of the entire haematopoietic system can be realized without too much stress on the non-haemotopoietic organs.

A comparable radioactivity distribution was realized with a radioimmuno conjugate consisting of a MAb of the type having a V-region as defined in the Sequence Listing, to which the radio nuclide is coupled via a bifunctional complex forming agent (isothiocyanatebenzyl-DPTA) (Camera et al., Eur. J. Nucl. Med., 21, 640–646, 1994). Radioimmuno conjugates of this kind, where the nuclide is coupled to the MAb by way of complex forming agents that are known from the literature, are also used to realize the advantageous distribution of radiation namely reaching highest activity in the bone marrow, as in Example 9. Accordingly, use of the radioimmuno conjugates according to the invention extend to all conjugates which, after systematic application, realize a preferential local radiation of the haematopoietic system.

Example 10

In Examples 1 to 9 the MAb according to the invention were linked with the β-radiators with the aid of complex forming agents and reducing agents.

Use of the following described materials and methods resulted in particularly stable complexes of Y-90 and MAb.

The non-reduced MAb was reacted with isocyanate citric acid or isothiocyanate-benzyl-citric acid or isothiocyanate-acetyl-citric acid under conditions that are known from the relevant literature (Meares et al: Analytical Biochemistry, 142, 98–78, 1984).

The resulting MAb-citric acid conjugate is then separated from the lower molecular contaminants by means of PD gel permeation chromatography (Pharmacia Biotech AB, Uppsala Sweden) according to the methods known from the relevant literature (Safavy et al. Bioconjugate Chem. 10, 18–23, 1999 page 20).

From the so purified MAb-citric acid conjugate, 2 mg are mixed with 100 mCi carrier-free Y-90 chloride (activity concentration: 100 mCi/0.5 ml) and incubated for 10 minutes at room temperature, after which the nuclide has been quantitatively bonded to the MAb conjugate.

25–100 mCi of the radioimmuno conjugate which is used for bone marrow conditioning are diluted with 2 ml physiological sodium chloride solution and within 5 minutes intravenously administered to the patient.

Within 20 minutes of administering the dose, activity is detected in the organs as follows: 80% of activity in the bone marrow, 8% in the liver, 6% in the spleen, 2% in the lung and 4% in the kidneys. The activity which is bound to granulocytes circulating in the blood stream is being eliminated at a rate of 4%/24 hours.

The activity in the bone marrow remains until the nuclide decays. This local radiation of the bone marrow leads to a complete radio elimination of the pluripotent cells of the bone marrow.

Unlike the MAb-DPTA or MAb-DOPA chelates known from the relevant literature, which can behave like an immunogenic hapten carrier, the MAb-citric acid complex does not induce an immune response against the hapten.

A reduced MAb may also be used—in conjunction with thiomethyl-acetyl-citric acid, as well as the type of reduced MAb as described in the Examples 1 through 8 supra. Furthermore, instead of using mercaptoethanol, other reducing agents may also be used in the reduction of the MAb, preferably also certain phosphines.

Example 11

A MAb of the type having a V-region as disclosed in the Sequence Listing, was radiolabelled with α- or β-radiators in accordance with the description as set forth in Examples 1 or 2 or 3 or 4–10.

Twelve patients with acute myeloid leukemia (AML) respectively chronic myeloid leukemia (CML) were intravenously injected with 100 mCi of activity per application with fractionated doses administered once every week. The therapy is designed to destroy not only the leukemic blast population in the bone marrow and other organs, but in particular, to also destroy the pluripotent blood stem cells and thus to permit a healthy repopulation in the bone marrow. After conducting suitable cytological tests of bone marrow and blood, autologous and allogenic bone marrow cells and blood cells were transplanted in accordance with the known techniques into the so treated patients. The patients treated with radioimmuno conjugate-monotherapy accepted the bone marrow transplant to a much greater percentage (12 out of 12), than patients which were treated with the currently conventional standard therapy, i.e. toxic cytostatics (maximally 60%). The percentage rate of recurrence under the radioimmuno conjugate-monotherapy is markedly reduced, as compared with the recurrence rate of treatment with cytostatics. The reason for these superior effects is the more specific and more efficacious destruction by the radiation energy of blood stem cells in the bone marrow from which the acute and myeloid leukemia originate.

The therapeutic effects become clear by the following dose distribution in the patient

TABLE 1

| Organ | Total Dose |
|---|---|
| Bone Marrow | 15–20 |
| Liver | 3–5 |
| Kidney | 5–7 |

In this therapy, the target organ is the bone marrow, a radio sensitive organ where approximately 80% of the administered radiation dose resides while the liver and kidneys, which are relatively insensitive to radiation, are only burdened insubstantially. In contrast, with the cytostatic therapy, the highly toxic cytostatics are distributed throughout the body in an unspecific way, which results in greater burdening of the essential organs such as liver, kidneys and lungs while only treating the target organ.

Example 12

A MAb of the type having a V-region as disclosed in the was radiolabelled with α- or β-radiators in accordance with the description as set forth in Examples 1 or 2 or 3 or 4–10.

Six patients, each with acute lymphatic leukemia (ALL) and 8 patients with chronic lymphatic leukemia (CLL) were intravenously injected with 100 mCi of activity per application with fractionated doses administered once every week for two weeks (100 mCi/week×2).

In the third week, the patients were treated with whole body irradiation (12 Gray) in addition to treatment with busulphan. After conducting suitable cytological tests of bone marrow and blood, autologous and/or more allogenic bone marrow cells and blood cells were transplanted in accordance with the known techniques into the so treated patients. 14 out of 14 patients treated with the combination therapy which consisted of radioimmuno therapy, whole body irradiation and chemotherapy went into complete remission. The recurrence free period was extended from 6 months to more than 9 months.

Unlike the treatment of AML and CML which can be treated with radioimmuno-monotherapy, treatment of ALL and CLL, in addition to treatment of the bone marrow, must include therapy of the lymphatic system (lymph nodes) due to the different distribution of malignancies. This was accomplished with supplemental whole body irradiation and chemotherapy.

Example 13

A MAb of the type having a V-region as disclosed in the Sequence Listing was radiolabelled with α- or β-radiators in accordance with the description as set forth in Examples 1 or 2 or 3 or 4–10.

Thirteen patients, each with acute lymphatic leukemia (ALL) and 12 patients, each with chronic lymphatic leukemia (CLL) were intravenously injected with 50 mCi of activity per application with fractionated doses administered once every week for two weeks (50 mCi/week×2). At the same time, the patients were injected with anti CD 20 MAb (RituxiMAb) which was radio labeled according to Examples either 1 or 2 or 3 or 4–10 with α- or β-radiators. After conducting suitable cytological tests of bone marrow and blood, autologous and allogenic bone marrow cells and blood cells were transplanted in accordance with the known techniques into the so treated patients. As a result, 80% (20 out of 25) of the patients went into complete remission. This high remission rate was solely due to the combination therapy with anti B-cells and anti granulocyte. MAb, which facilitated efficacious radiation of the lymph nodes and the bone marrow.

Example 14

A bispecific MAb, selective for lymphocytes, granulocytes or granulocyte precursors was prepared according to the known techniques disclosed in EP 0 517 024 B1 and was labeled in accordance with the method described in the above Examples 1 or 2 or 3 or 4–10 with α- or β-radiators. 8 Patients, each with acute lymphatic leukemia and 12 patients, each with chronic lymphatic leukemia were intravenously injected with 100 mCi of activity per application administered once every week for two weeks (100 mCi/week×2). After conducting suitable cytological tests of bone marrow and blood, autologous and/or allogenic bone marrow cells and blood cells were transplanted in accordance with the known techniques into the so treated patients.

As a result, 90% (18 out of 20) of the patients went into complete remission. This high remission rate was solely due to the bispecificity of the construct which facilitated efficient radiation of the lymph nodes and the bone marrow.

Example 15

A MAb of the type having a V-region as disclosed in the Sequence Listing was radiolabelled with α- or β-radiators in accordance with the description as set forth in Examples 1 or 2 or 3 or 4–10.

Three patients, each with acute and/or chronic lymphatic leukemia were intravenously injected with 100 mCi of activity per application. 1 to 4 hours after injection of the immuno conjugate, the patient was intravenously injected with a toxicologically negligible dose (20 mg per kg body weight of the patient) of disodium calcium EDTA (e.g. Edtacal) or preferably calcium-DPTA (e.g. ditipentate) or zinc-DPTA or calciummercapto succinic acid or another toxicologically negligible complex forming agent. This induces the elimination of the free nuclide derived from the radioimmuno conjugate, from all extracellular compartments through the urinary system. This serves to reduce the unspecific radiation dose from the normal body tissue. Suitable cytological tests were carried out thereafter. Further therapeutic steps are carried out as described in Example 11.

Example 16

A MAb of the type having a V-region as disclosed in the Sequence Listing was radiolabelled with α- or β-radiators (radioimmuno conjugate) in accordance with the description as set forth in examples 1 or 2 or 3 or 4 to 10.

Four patients, each with malignant pemphigus were intravenously injected with a radioimmuno conjugate having an activity of 100 mCi per application in fractionated doses once every week. 1 to 4 hours after injection of the radioimmuno conjugate, the patient was intravenously injected with a toxicologically negligible dose (20 mg per kg body weight of the patient) of disodium calcium EDTA (e.g. Edtacal) or preferably calcium-DPTA (e.g. ditipentate) or zinc-DPTA or calcium-mercapto succinic acid or another toxicologically negligible complex forming agent. This treatment induces the elimination of the free nuclide derived from the radioimmuno conjugate, from all extracellular compartments through the urinary system. This serves to reduce the unspecific radiation dose from the normal body tissue. Patients that were treated with this radioimmuno conjugate mono-therapy all accepted the bone marrow transplant. After several weeks, the symptoms of the pemphigus had disappeared.

Example 17

A MAb of the type having a V-region as disclosed in the Sequence Listing was radiolabelled with α- or β-radiators (radioimmuno conjugate) in accordance with the description as set forth in examples 1 or 2 or 3 or 4–10.

Two female patients, each with progressive metastasized mamma carcinoma and osseous metastases were intravenously injected with fractionated doses once a week for two weeks with a radioimmuno conjugate having a radioimmuno activity of 100 mCi per application (100 mCi/week×2). Thereafter, each of these patients were treated with a high dose chemotherapy followed by a bone marrow transplant. Both patients accepted the bone marrow. The osseous metastases were quantitatively eliminated and both patients went into complete remission.

Example 18

A MAb of the type having a V-region as disclosed in the Sequence Listing was radiolabelled with α- or β-radiators (radioimmuno conjugate) in accordance with the description as set forth in Examples 1 or 2 or 3 or 4–10.

Three patients, each with non-hormone dependent metastasizing prostate carcinoma and osseous metastases were intravenously injected with fractionated doses once a week for two weeks with a radioimmuno conjugate having a radioimmuno conjugate activity of 100 mCi per application (100 mCi/week×2). Thereafter, each patient received bone marrow transplant. All three patients accepted the bone marrow. The osseous metastases were quantitatively removed.

Example 19

A MAb of the type having a V-region as disclosed in the Sequence Listing was radiolabelled with α- or β-radiators (radioimmuno conjugate) in accordance with the description as set forth in Examples 1 or 2 or 3 or 4–10.

Two patients with advanced non-Hodgkin's lymphoma spreading into the bone marrow, were intravenously injected with fractionated doses once a week for two weeks with a radioimmuno conjugate having a radioimmuno conjugate activity of 100 mCi per application. Thereafter, each of the patients were treated with high dose chemotherapy followed by a bone marrow transplant. Both patients accepted the bone marrow. After this treatment, no further lymphoma metastases could be detected in the bone marrow.

Example 20

A MAb of the type having a V-region as disclosed in the Sequence Listing was radiolabelled with α- or β-radiators (radioimmuno conjugate) in accordance with the description as set forth in Examples 1 or 2 or 3 or 4–10.

One patient each, with bone marrow metastases of lung carcinoma, mamma carcinoma, prostate carcinoma, pancreas carcinoma, stomach carcinoma, liver carcinoma, kidney carcinoma, colon carcinoma, rectal carcinoma, testicular tumors, ovarian carcinoma, melanoma, lymphoma, mesotheliom, Kaposi sarcoma, haemangiom, sarcoma, osteosarcoma, bladder carcinoma, and nose-, throat and ear-carcinomas, were intravenously injected with fractionated doses once a week for two weeks with radioimmuno conjugate having a radioimmuno conjugate activity of 100 mCi per application. After a bone marrow transplant, in none of these patients metastases in the bone marrow were detected.

Example 21

According to the current level of bone marrow transplant techniques, patients which are scheduled for a transplant, are treated prior to the transplant, for example, with whole body irradiation in order to sufficiently condition the bone marrow in these patients. Since the radiation affects also normal body tissue, such treatments are accompanied by severe side effects. Accordingly, three patients scheduled for bone marrow transplant were intravenously injected with radioimmuno conjugate having activity of 100 mCi as described in Example 20, once a week for two weeks. Subsequently, each patient received an allogenic bone marrow transplant. All three patients accepted the bone marrow. Side effects that were observed were limited to nausea, light vomiting, loss of appetite in 50% of the patients, WHO Grad I/II. No mucous membrane damage, nor vascular problems were observed.

Example 22

A MAb of the type having a V-region as disclosed in the Sequence Listing was labelled in accordance with the methods known from the relevant literature with biotin. The low molecular biotin which did not bind to the MAb was separated via a Sephadex G-20 column.

Two patients, each with AML and 2 patients, each with CML, were intravenously injected with 100 mg MAb-biotin conjugate. After a period of 5 to 10 days the patients were injected each with 100 mCi avidin, which was labeled with α- or β-radiators in accordance with the methods as described in Examples 1–8 supra. This two phase method permits that an even higher dose of radiation is deposited in the leukemic bone marrow than can be achieved with the therapy where the radioimmuno conjugate is applied solely to the target tissue. All four patients went into a complete remission.

The advantage of this treatment method as compared to the one-phase therapy treatment with a radioimmuno conjugate is that, by administering high doses of MAb-biotin conjugate, saturation of the binding sites on cells in the haematopoietic system may be realized. Injections with radio labelled avidin that then follow, result in a very efficacious localization at the MAb-biotin conjugate of the avidin, due to the high avidity of the avidin to the MAb-biotin conjugate, that is, within the leukemic bone marrow. With this technique, an advantageous in vivo system for the two-phase immuno conjugate therapy is realized, which administers even higher doses of radiation to the target tissue than with the above described one-phase radioimmuno conjugate therapy (radioimmuno conjugate). The avidin can also be replaced with other avidin binding molecules such as, for example, streptavidin or fragments of such avidin binding molecules that have been produced by recombinant, biochemical or peptid chemical methods.

Alternatively, a humanized variant of the MAb, as well as functionally equivalent MAb which bind to the cells of the haematopoietic system can be used. When humanizing is desired, the CDR (complementary determining regions or hyper variable regions) is transplanted by recombinant methods onto a human V-gene frame work. Sequences originating from the mouse V-region, CDR cDNA sequences are used and are set forth in the Sequence Listing Nos. 5, 7, 9, 11, 13 and 15.

While the invention has been illustrated and described as embodied in a radioimmuno conjugate, it is not intended to be limited to the details shown since various modifications and changes may be made without departing in any way from the spirit of the present invention.

SEQUENCE LISTING

SEQ. ID NO. 1
Sequence Protocol:
Type of Sequence:           nucleotide with respective protein
Length of Sequence:         357 base pairs
Form:                       single strand
Topology:                   linear
Type of Molecule:           cDNA to mRNA
Original Origin of Organism: mouse Features:

cDNA sequence of cordons for amino acids 1–119 of VH exon for the heavy chain gene which codes for the MAb heavy chain and the amino acid sequence associated therewith. Amino acids are numbered according to Wu and Kabat

```
VH
 1                         5                        10                       15
CAG GTC CAA CTG CAG GAG TCT GGA GGA GGC TTG GTA CAG CCT GGG GGT
Gln Val Gln Leu Gln Glu Ser Gly Gly Gly Leu Val Gln Pro Gly Gly 20                        25                       30
TCT CTG AGA CTC TCC TGC GCA ACT TCT GGG TTC AGT GAT TAC TAC ATG
Ser Leu Arg Leu Ser Cys Ala Thr Ser Gly Phe Ser Asp Tyr Tyr Met 35                        40                        45
AAC TGG GTC CGC CAG CCT CCA GGA AAA GCA CTT GAG TGG TTG GGT TTT
Asn Trp Val Arg Gln Pro Pro Gly Lys Ala Leu Glu Trp Leu Gly Phe 50                        52                        60
AAT TCA AAC AAA CCT AAT GGT CAC ACA ACA GAG TAC AGT GCA TCT GTG
Ile Ser Asn Lys Pro Asn Gly His Thr Thr Glu Tyr Ser Ala Ser Val 65                        70                        75                       80
AAG GGT CGG TTC ACC ATC TCC AGA GAT AAT TCC CAA AGC ATC CTC TAT
Lys Gly Arg Phe Thr Ile Ser Arg Asp Asn Ser Gln Ser Ile Leu Tyr 85                        90                       95
CTT CAA ATG AAC ACC CTG AGA GCT GAG GAC AGT GCC ACT TAT TAT TGT
Leu Gln Met Asn Thr Leu Arg Ala Glu Asp Ser Ala Thr Tyr Tyr Cys 100                       105                      110
GCA AGA GAT AAG GGA ATA CGA TGG TAC TTC GAT GTC TGG GGC CAA GGG
Ala Arg Asp Lys Gly Ile Arg Trp Tyr Phe Asp Val Trp Gly Gln Gly

115
ACC ACG GTC ACC GTC TCC TCA
Thr Thr Val Thr Val Ser Ser
```

SEQ. ID NO. 2
Sequence Protocol:
Type of Sequence:           nucleotide with respective protein
Length of Sequence:         292 base pairs
Form:                       single strand
Topology:                   linear
Type of Molecule:           cDNA to mRNA
Original Origin of Organism: mouse cDNA sequence of codons for amino acids 9–105 of VL exon for κ-light chain gene (VK) which codes for the MAb light chain and the amino acid sequence associated therewith. Amino acids are numbered according to Wu and Kabat.

```
VK
        10                    15                    20
A GCA ATC CTG TCT GCA TCT CCA GGG GAG AAG CTG ACA ATG ACT TGC
  Ala Ile Leu Ser Ala Ser Pro Gly Glu Lys Val Thr Met Thr Cys 25                    30                    35
AGC GCC AGC TCA AGT GTA AGT TAC ATG CAC TGG TAC CAG CAG AAG CCA
Arg Ala Ser Ser Ser Val Ser Tyr Met His Trp Tyr Gln Gln Lys Pro 40                    45                    50                55
GGA TCC TCC CCC AAA CCC TGG ATT TAT GCC ACA TCC AAC CTG GCT TCT
Gly Ser Ser Pro Lys Pro Trp Ile Tyr Ala Thr Ser Asn Leu Ala Ser 60                    65                    70
GGA GTC CCT GCT CGC TTC AGT GGC AGT GGG TCT GGG ACC TCT TAC TCT
Gly Val Pro Ala Arg Phe Ser Gly Ser Gly Ser Gly Thr Ser Tyr Ser 75                    80                    85
CTC ACA ATC ATC AGA GTG GAG GCT GAA GAT GCT GCC ACT TAT TAC TGC
Leu Thr Ile Ile Arg Val Glu Ala Glu Asp Ala Ala Thr Tyr Tyr Cys 90                    95                  100
CAG CAG TGG AGT AGT AAC CCG CTC ACG TTC GGT GCT GGG ACC AAG CTG
Gln Gln Trp Ser Ser Asn Pro Leu Thr Phe Gly Ala Gly Thr Lys Leu

105
GAG ATC
Glu Ile
```

Alternatively, a humanized variant of the MAb, as well as functionally equivalent MAb which bind to the cells of the haematopoietic system can be used. When humanizing is desired, the following CDR (complementary determining regions or hyper variable regions) is transplanted by recombinant methods onto a human V-gene frame work. The following sequences originating from the mouse V-region CDR cDNA sequences are used.

```
VH, CDR1:                                                         SEQ ID NO. 3
GAT TAC TAC ATG AAC
Asp Tyr Tyr Met Asn

VH, CDR2:                                                         SEQ ID NO. 4
TTT ATT TCA AAC AAA CCT AAT GGT CAC ACA ACA GAG TAC GTA GCA TCT
Phe Ile Ser Asn Lys Pro Asn Gly His Thr Thr Glu Tyr Val Ala Ser

GTG AAG GGT
Val Lys Gly

VH, CDR3:                                                         SEQ ID NO. 5
GAT AAG GGA ATA CGA TGG TAC TTC GAT GTC
Asp Lys Gly Ile Arg Trp Tyr Phe Asp Val

VK, CDR1:                                                         SEQ ID NO. 6
AGG GCC AGC TCA AGT GTA AGT TAC ATG CAC
Arg Ala Ser Ser Ser Val Ser Tyr Met His

VK, CDR2:                                                         SEQ ID NO. 7
GCC ACA TCC AAC CTG GTC TCT
Ala Thr Ser Asn Leu Ala Ser

VK, CDR3:                                                         SEQ ID NO. 8
CAG CAG TGG AGT AGT AAC CCG CTC ACG
Gln Gln Trp Ser Ser Asn Pro Leu Thr
```

What is claimed is:

1. A method for irradiating bone marrow of a patient in the treatment of haematopoietic diseases comprising, administering to the patient an effective dose of a radioimmuno conjugate consisting essentially of a monoclonal antibody or antibody fragments having a binding specificity which is selective for CD 66 a, b, c, e and a radioisotope which is one of an α-radiator or a β radiator, the radioisotope; and wherein the radioisotope is stably coupled to the antibody.

2. The method of claim 1, wherein the Mab of the immuno conjugate has a variable region sequence as identified in SEQ. ID 1–8.

3. The method of claim 1, wherein the β-radiator is an isotope selected from the group consisting of Yttrium-90, Rhenium-188, Rhenium-186, Copper-67, Holmium-166 or Samarium-153.

4. The method of claim 1, wherein the α-radiator is an isotope selected from the group consisting of Astatine-211 or Bismuth-212.

5. The method of claim 1, wherein the radioimmuno conjugate is administered to the patient in a dose sufficient to attain a radiation distribution of about 8% in the liver, about 2% in the lung, about 6% in the spleen, about 4% in the kidneys, not less than 30% in the bone marrow.

6. The method of claim 1, wherein the radioimmuno conjugate is administered to the patient in conjunction with one or more therapies selected from the group consisting of chemotherapy, bone marrow transplant or total body irradiation therapy.

7. The method of claim 1, wherein the patient is treated for one or more diseases selected from the group consisting of malignant pemphigus, chronic myeloid leukemia, acute myeloid leukemia, bone marrow metastases of lung carcinoma, mamma carcinoma, pancreas carcinoma, stomach carcinoma, liver carcinoma, kidney carcinoma, colon carcinoma, rectal carcinoma, testicular carcinoma, ovarian carcinoma, melanoma, lymphoma, mesotheliom, Kaposi sarcoma, haemangiom, sarcoma, osteosarcoma, bladder carcinoma, and nose-, throat-and ear-tumors.

8. The method of claim 1, wherein the effective dose of radioimmuno conjugate is sufficient to deplete the patient's bone marrow cells.

9. A radioimmuno conjugate for conditioning the bone marrow of a patient comprising, an antibody, (Mab), which is selective for an epitope or epitopes on CD 66 a, b, c, e.

a radioisotope selected from the group consisting of α-radiator and β-radiator, said radioisotope being stably coupled to the antibody to form a conjugate, without a complex forming agent or with a low or non-immunogenic complex forming agent.

10. The radioimmuno conjugate of claim 8, wherein the Mab has a variable region as specified in SEQ. ID 1–8.

* * * * *

SEQUENCE LISTING

<160> NUMBER OF SEQ ID NOS: 16

<210> SEQ ID NO: 1
<211> LENGTH: 357
<212> TYPE: DNA
<213> ORGANISM: Mus musculus
<220> FEATURE:
<223> OTHER INFORMATION: cDNA sequence of codons for amino acids 1-119
      of VH exon for heavy chain gene which codes for the
      MAb heavy chain and the amino acid sequence
      associated therewith
<220> FEATURE:
<221> NAME/KEY: CDS
<222> LOCATION: (1)..(357)

<400> SEQUENCE: 1

```
cag gtc caa ctg cag gag tct gga gga ggc ttg gta cag cct ggg ggt      48
Gln Val Gln Leu Gln Glu Ser Gly Gly Gly Leu Val Gln Pro Gly Gly
  1               5                  10                  15 tct ctg aga ctc tcc tgc gca act tct ggg ttc agt gat tac tac atg      96
Ser Leu Arg Leu Ser Cys Ala Thr Ser Gly Phe Ser Asp Tyr Tyr Met
             20                  25                  30 aac tgg gtc cgc cag cct cca gga aaa gca ctt gag tgg ttg ggt ttt     144
Asn Trp Val Arg Gln Pro Pro Gly Lys Ala Leu Glu Trp Leu Gly Phe
         35                  40                  45 att tca aac aaa cct aat ggt cac aca aca gag tac agt gca tct gtg     192
Ile Ser Asn Lys Pro Asn Gly His Thr Thr Glu Tyr Ser Ala Ser Val
     50                  55                  60 aag ggt cgg ttc acc atc tcc aga gat aat tcc caa agc atc ctc tat     240
Lys Gly Arg Phe Thr Ile Ser Arg Asp Asn Ser Gln Ser Ile Leu Tyr
 65                  70                  75                  80 ctt caa atg aac acc ctg aga gct gag gac agt gcc act tat tat tgt     288
Leu Gln Met Asn Thr Leu Arg Ala Glu Asp Ser Ala Thr Tyr Tyr Cys
                 85                  90                  95 gca aga gat aag gga ata cga tgg tac ttc gat gtc tgg ggc caa ggg     336
Ala Arg Asp Lys Gly Ile Arg Trp Tyr Phe Asp Val Trp Gly Gln Gly
            100                 105                 110 acc acg gtc acc gtc tcc tca                                         357
Thr Thr Val Thr Val Ser Ser
        115
```

<210> SEQ ID NO: 2
<211> LENGTH: 119
<212> TYPE: PRT
<213> ORGANISM: Mus musculus

<400> SEQUENCE: 2

```
Gln Val Gln Leu Gln Glu Ser Gly Gly Gly Leu Val Gln Pro Gly Gly
  1               5                  10                  15

Ser Leu Arg Leu Ser Cys Ala Thr Ser Gly Phe Ser Asp Tyr Tyr Met
             20                  25                  30

Asn Trp Val Arg Gln Pro Pro Gly Lys Ala Leu Glu Trp Leu Gly Phe
         35                  40                  45

Ile Ser Asn Lys Pro Asn Gly His Thr Thr Glu Tyr Ser Ala Ser Val
     50                  55                  60

Lys Gly Arg Phe Thr Ile Ser Arg Asp Asn Ser Gln Ser Ile Leu Tyr
 65                  70                  75                  80

Leu Gln Met Asn Thr Leu Arg Ala Glu Asp Ser Ala Thr Tyr Tyr Cys
                 85                  90                  95

Ala Arg Asp Lys Gly Ile Arg Trp Tyr Phe Asp Val Trp Gly Gln Gly
```

-continued

```
                    100                 105                 110
Thr Thr Val Thr Val Ser Ser
            115

<210> SEQ ID NO: 3
<211> LENGTH: 292
<212> TYPE: DNA
<213> ORGANISM: Mus musculus
<220> FEATURE:
<223> OTHER INFORMATION: cDNA sequence of codons for amino acids 9-105
      of VL exon for k-light chain gene (VK) which codes
      for the MAb light chain and the amino acid
      sequence associated therewith
<220> FEATURE:
<221> NAME/KEY: CDS
<222> LOCATION: (2)..(292)

<400> SEQUENCE: 3 a gca atc ctg tct gca tct cca ggg gag aag gtc aca atg act tgc agc       49
  Ala Ile Leu Ser Ala Ser Pro Gly Glu Lys Val Thr Met Thr Cys Ser
   1               5                  10                  15 gcc agc tca agt gta agt tac atg cac tgg tac cag cag aag cca gga        97
Ala Ser Ser Ser Val Ser Tyr Met His Trp Tyr Gln Gln Lys Pro Gly
                20                  25                  30 tcc tcc ccc aaa ccc tgg att tat gcc aca tcc aac ctg gct tct gga       145
Ser Ser Pro Lys Pro Trp Ile Tyr Ala Thr Ser Asn Leu Ala Ser Gly
            35                  40                  45 gtc cct gct cgc ttc agt ggc agt ggg tct ggg acc tct tac tct ctc       193
Val Pro Ala Arg Phe Ser Gly Ser Gly Ser Gly Thr Ser Tyr Ser Leu
        50                  55                  60 aca atc atc aga gtg gag gct gaa gat gct gcc act tat tac tgc cag       241
Thr Ile Ile Arg Val Glu Ala Glu Asp Ala Ala Thr Tyr Tyr Cys Gln
 65                  70                  75                  80 cag tgg agt agt aac ccg ctc acg ttc ggt gct ggg acc aag ctg gag       289
Gln Trp Ser Ser Asn Pro Leu Thr Phe Gly Ala Gly Thr Lys Leu Glu
                85                  90                  95 atc                                                                   292
Ile

<210> SEQ ID NO: 4
<211> LENGTH: 97
<212> TYPE: PRT
<213> ORGANISM: Mus musculus

<400> SEQUENCE: 4

Ala Ile Leu Ser Ala Ser Pro Gly Glu Lys Val Thr Met Thr Cys Ser
 1               5                  10                  15

Ala Ser Ser Ser Val Ser Tyr Met His Trp Tyr Gln Gln Lys Pro Gly
                20                  25                  30

Ser Ser Pro Lys Pro Trp Ile Tyr Ala Thr Ser Asn Leu Ala Ser Gly
            35                  40                  45

Val Pro Ala Arg Phe Ser Gly Ser Gly Ser Gly Thr Ser Tyr Ser Leu
        50                  55                  60

Thr Ile Ile Arg Val Glu Ala Glu Asp Ala Ala Thr Tyr Tyr Cys Gln
 65                  70                  75                  80

Gln Trp Ser Ser Asn Pro Leu Thr Phe Gly Ala Gly Thr Lys Leu Glu
                85                  90                  95

Ile

<210> SEQ ID NO: 5
<211> LENGTH: 15
```

```
<212> TYPE: DNA
<213> ORGANISM: Mus musculus
<220> FEATURE:
<221> NAME/KEY: CDS
<222> LOCATION: (1)..(15)
<223> OTHER INFORMATION: VH Complementary determining regions or hyper
      variable region CDR1

<400> SEQUENCE: 5 gat tac tac atg aac                                                    15
Asp Tyr Tyr Met Asn
 1               5

<210> SEQ ID NO: 6
<211> LENGTH: 5
<212> TYPE: PRT
<213> ORGANISM: Mus musculus

<400> SEQUENCE: 6

Asp Tyr Tyr Met Asn
 1               5

<210> SEQ ID NO: 7
<211> LENGTH: 57
<212> TYPE: DNA
<213> ORGANISM: Mus musculus
<220> FEATURE:
<221> NAME/KEY: CDS
<222> LOCATION: (1)..(57)
<223> OTHER INFORMATION: VH CDR2 Complementary determining or hyper
      variable regions

<400> SEQUENCE: 7 ttt att tca aac aaa cct aat ggt cac aca aca gag tac gta gca tct        48
Phe Ile Ser Asn Lys Pro Asn Gly His Thr Thr Glu Tyr Val Ala Ser
 1               5                  10                  15 gtg aag ggt                                                            57
Val Lys Gly <210> SEQ ID NO: 8
<211> LENGTH: 19
<212> TYPE: PRT
<213> ORGANISM: Mus musculus

<400> SEQUENCE: 8

Phe Ile Ser Asn Lys Pro Asn Gly His Thr Thr Glu Tyr Val Ala Ser
 1               5                  10                  15

Val Lys Gly

<210> SEQ ID NO: 9
<211> LENGTH: 30
<212> TYPE: DNA
<213> ORGANISM: Mus musculus
<220> FEATURE:
<221> NAME/KEY: CDS
<222> LOCATION: (1)..(30)
<223> OTHER INFORMATION: VH CDR3 Complementary determining regions  or
      hyper variable regions

<400> SEQUENCE: 9 gat aag gga ata cga tgg tac ttc gat gtc                                30
Asp Lys Gly Ile Arg Trp Tyr Phe Asp Val
 1               5                  10

<210> SEQ ID NO: 10
<211> LENGTH: 10
<212> TYPE: PRT
```

```
<213> ORGANISM: Mus musculus

<400> SEQUENCE: 10

Asp Lys Gly Ile Arg Trp Tyr Phe Asp Val
 1               5                  10

<210> SEQ ID NO: 11
<211> LENGTH: 30
<212> TYPE: DNA
<213> ORGANISM: Mus musculus
<220> FEATURE:
<221> NAME/KEY: CDS
<222> LOCATION: (1)..(30)
<223> OTHER INFORMATION: VK CDR1 Complenetrary determining regions or
      hyper variable regions

<400> SEQUENCE: 11 agg gcc agc tca agt gta agt tac atg cac                          30
Arg Ala Ser Ser Ser Val Ser Tyr Met His
 1               5                  10

<210> SEQ ID NO: 12
<211> LENGTH: 10
<212> TYPE: PRT
<213> ORGANISM: Mus musculus

<400> SEQUENCE: 12

Arg Ala Ser Ser Ser Val Ser Tyr Met His
 1               5                  10

<210> SEQ ID NO: 13
<211> LENGTH: 21
<212> TYPE: DNA
<213> ORGANISM: Mus musculus
<220> FEATURE:
<221> NAME/KEY: CDS
<222> LOCATION: (1)..(21)
<223> OTHER INFORMATION: VK CDR2 Complementary determining regions or
      variable regions

<400> SEQUENCE: 13 gcc aca tcc aac ctg gct tct                                      21
Ala Thr Ser Asn Leu Ala Ser
 1               5

<210> SEQ ID NO: 14
<211> LENGTH: 7
<212> TYPE: PRT
<213> ORGANISM: Mus musculus

<400> SEQUENCE: 14

Ala Thr Ser Asn Leu Ala Ser
 1               5

<210> SEQ ID NO: 15
<211> LENGTH: 27
<212> TYPE: DNA
<213> ORGANISM: Mus musculus
<220> FEATURE:
<221> NAME/KEY: CDS
<222> LOCATION: (1)..(27)
<223> OTHER INFORMATION: VK CDR3 Complementary determining regions or
      hyper variable regions

<400> SEQUENCE: 15 cag cag tgg agt agt aac ccg ctc acg                              27
Gln Gln Trp Ser Ser Asn Pro Leu Thr
 1               5
```

```
<210> SEQ ID NO: 16
<211> LENGTH: 9
<212> TYPE: PRT
<213> ORGANISM: Mus musculus

<400> SEQUENCE: 16

Gln Gln Trp Ser Ser Asn Pro Leu Thr
 1               5
```